United States Patent [19]

Hahn et al.

[11] Patent Number: 5,176,710
[45] Date of Patent: Jan. 5, 1993

[54] PROSTHESIS WITH LOW STIFFNESS FACTOR

[75] Inventors: Dustan L. Hahn, Derby; David A. McQueen; C. Douglas Pence, both of Wichita, all of Kans.

[73] Assignee: Orthopaedic Research Institute, Wichita, Kans.

[21] Appl. No.: 873,631

[22] Filed: Apr. 20, 1992

Related U.S. Application Data

[63] Continuation of Ser. No. 644,893, Jan. 23, 1991, abandoned.

[51] Int. Cl.⁵ .......................... A61F 2/38; A61F 2/30
[52] U.S. Cl. ........................ 623/20; 623/16; 623/18
[58] Field of Search .............................. 623/16, 18, 20

[56] References Cited

U.S. PATENT DOCUMENTS

| Re. 29,757 | 9/1978 | Helfet | 623/20 |
| 3,986,212 | 10/1976 | Sauer | 623/18 |
| 4,164,794 | 8/1979 | Spector et al. | 623/22 |
| 4,195,368 | 4/1980 | Patrichi | 623/18 |
| 4,502,161 | 3/1985 | Wall | 623/18 |
| 4,662,887 | 5/1987 | Turner et al. | 623/16 |
| 4,769,040 | 9/1988 | Wevers | 623/20 |
| 4,778,472 | 10/1988 | Homsy et al. | 623/18 |
| 4,808,185 | 2/1989 | Penenberg et al. | 623/20 |

Primary Examiner—Ronald Frinks
Attorney, Agent, or Firm—Hovey, Williams, Timmons & Collins

[57] ABSTRACT

An orthopaedic device designed to replace an articulating surface in a joint is provided. The device has a relatively low stiffness factor and is capable of applying normal physiological load onto the underlying bone. A low stiffness factor is achieved by a relatively thin device made from materials that have a low bulk modulus of elasticity. The device is provided with curvature to minimize bending stress in the device so that the device has sufficient mechanical strength to prevent stress induced failure. A tibial component made in accordance with this invention is also provided.

15 Claims, 1 Drawing Sheet

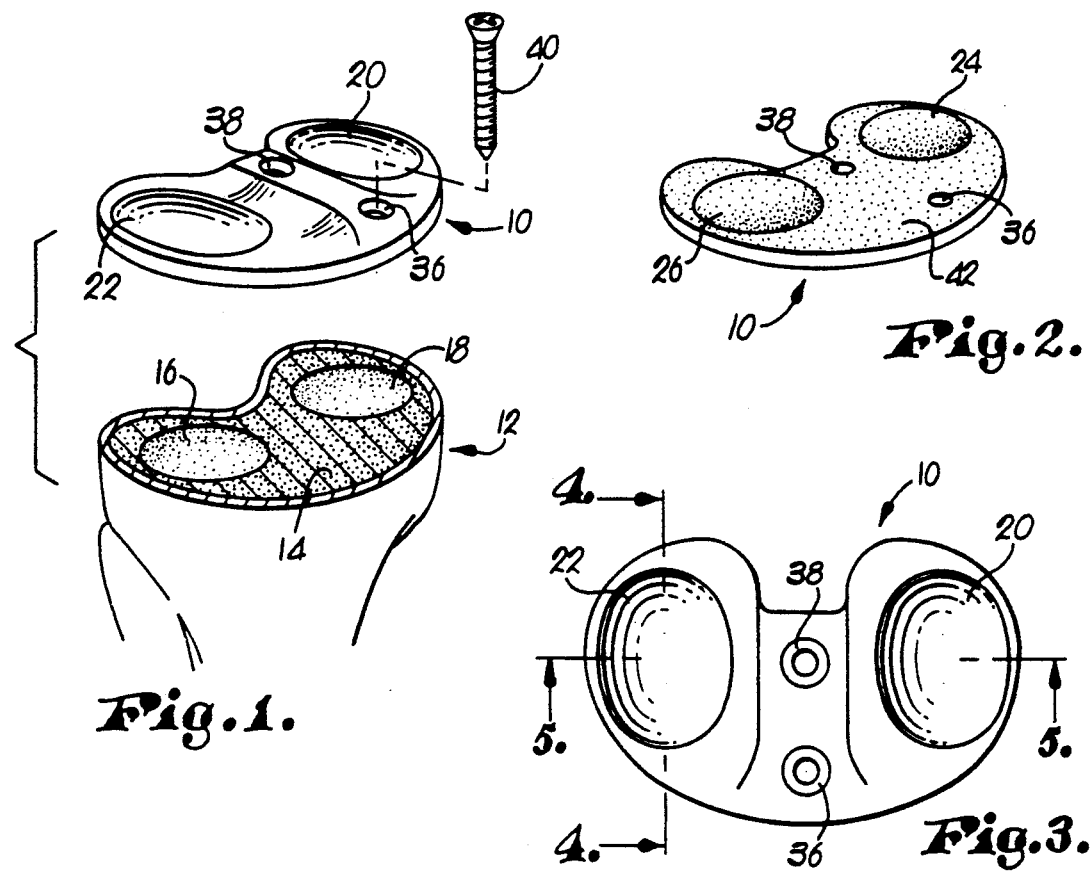
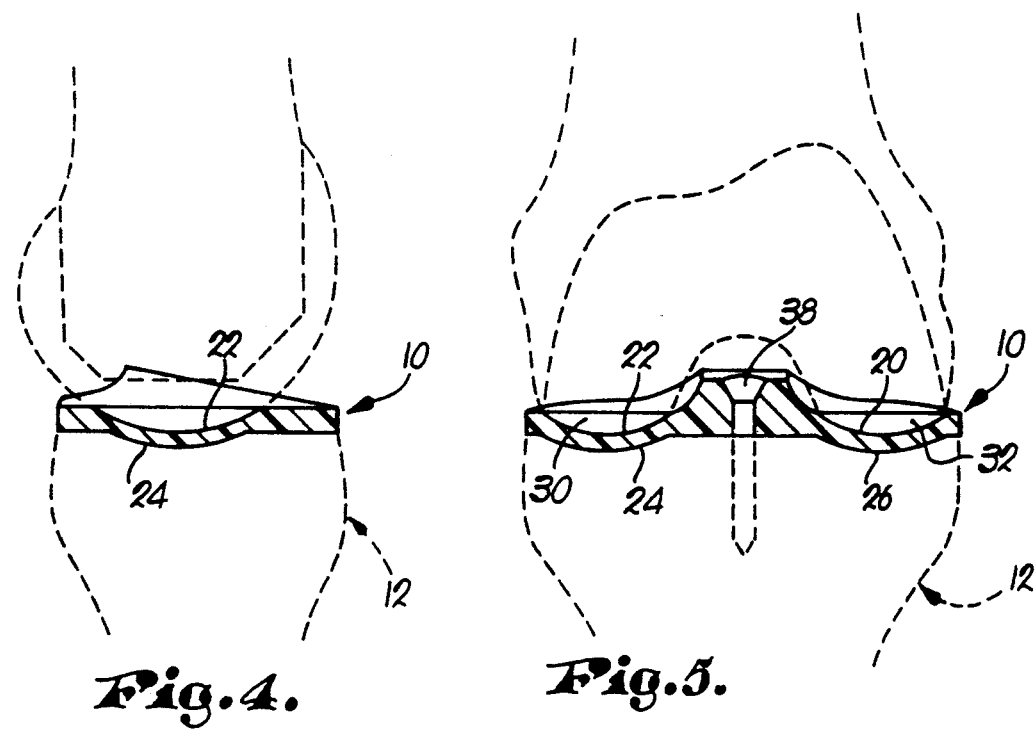

PROSTHESIS WITH LOW STIFFNESS FACTOR

This application is a continuation of application Ser. No. 07/644,893, filed Jan. 23, 1991, now abandoned.

BACKGROUND AND SUMMARY OF THE INVENTION

This invention relates to an orthopaedic surgical implant device or prosthetic component useful for long-term replacement of an articulating surface in a joint.

The articulating or bearing surfaces of bones in a joint are particularly susceptible to deterioration caused by injury or disease which leads to loss of movement and severe pain. It is generally known to surgically remove the damaged bone in a joint and attach a prosthetic component onto the resected bone surface wherein the component is anatomically designed to closely replicate the natural form and function of the articulating surface.

Consider by way of example, the surgical restoration of the knee joint often referred to as total knee arthroplasty. Total knee arthroplasty (TKA) is a surgical procedure wherein the damaged bone surfaces of the knee joint are removed and replaced with implant devices which facilitate accurate articulation at the restored joint so that a full range of motion including extension, flexion and some rotation in the joint is possible. To achieve normal movement in the joint, a separate component for the femur, tibia and patella corresponding in configuration to the natural articulating surface of the bones respectively is provided.

It is known to fabricate the aforementioned prosthetic components from high strength metallic materials such as titanium or chrome-cobalt which are known to exhibit biocompatibility. The metallic component is directly attached to the resected bone surface by a variety of methods. A plastic component is provided at the interface of the metallic surfaces to lower friction. For example, in Total Knee Arthroplasty the patellar and tibial devices are metal-backed plastic components. The metallic surface of the component is attached directly onto the bone surface and distributes load onto the related bone. The low-friction plastic surface provides the bearing or articulation surface in contact with the other surfaces in the joint. The femoral component is a single metallic unit having a full range of motion in contact with the plastic bearing surfaces of the tibial and patellar components. Each implant device has screws, pegs, stems or other contrivance to aid in the fixation of the device to bone on a short-term or long-term basis. It is additionally known to secure the components to the bone with cement applied at the interface of the bone and prosthetic component. Newer art provides a means for firm attachment to the bone in the form of porous metallic or plastic coating on the attachment surface of the component which permits bone ingrowth.

Although the prior art implant devices have had success as functional replacements of removed tissue, it is known that over time the components tend to loosen. Component loosening may require further surgery to re-attach the component, or sometimes additional bone is removed and a new replacement component is attached. The tibial component, in particular, is known to experience component loosening over time which eventually leads to failure of the joint restoration.

Several tibial component designs have been developed to prevent loosening and component failure. More severe or harsh methods of attachment such as attaching the component onto the proximal end of the tibia with large spikes or posts have been used alone or in conjunction with cement. These designs are directed to preventing lateral or rotational movement of the component which may cause loosening over time. However, a large amount of bone must be removed to provide deep canals in the bone surface for the spikes or posts.

U.S. Pat. No. 4,808,185 issued to Penenberg, et al. discloses a tibial prosthesis developed to permanently fix the component to the bone. The distal surface of the implant device has domical contours which interengage and fit into corresponding domical recesses cut in the resected surface of the bone. Attachment is provided by screws placed through the component and into the proximal tibia at the domical recesses. A metallic coating as heretofore mentioned is also provided on the distal surface of the component to promote bone ingrowth. The component is designed to assure firm attachment to the bone by uniformly spreading forces through the tibia and preventing lateral movement of the component.

The prior art means have attempted to solve the problem of component failure by firmly attaching the component to bone, evenly distributing load across the surface of bone and preventing lateral or rotational movement of the component. However component loosening remains a problem, especially in the tibial replacements and further refinement is needed to improve implant longevity. In so doing the procedure could be offered to younger or more active patients who are presently not considered good candidates for TKA.

It is generally believed that one factor which contributes to component loosening and restoration failure is bone remodeling which prevents the bone from supporting the prosthetic component or patient activity level. The bone to which the prosthesis is attached is not a structurally homogeneous material, it has a wide range of mechanical properties. Bone has the ability to rearrange its entire structure in a pattern which will provide maximum strength while using a minimum of material. The resorption of old bone and generation of new bone occurs in a way which improves bone's ability to carry mechanical loads. Researchers have discovered that many of the design features incorporated in the tibial components including attachment means such as pegs and stems deleteriously alter the manner in which mechanical load is distributed. More importantly, the inventors have discovered that the relatively stiff implant devices of the prior art distribute load to the underlying bone differently than it is transferred by the natural bone. In the natural tibia, loads are transferred through the two condyles of the femur, to the medial and lateral regions on the tibial plateau. Analysis has shown that mechanical loads are applied to the natural intact proximal tibia in relatively localized areas. With current prosthetic devices, the stress in the proximal tibia is lower and more uniformly distributed. The relatively stiff component acts as a plate which distributes the load evenly across an elastic foundation. As the stiffness of the prosthesis is reduced, stress in the proximal tibia increases and as the stiffness of the component approaches that of bone, the stress in the proximal tibia approaches that of the intact natural tibia.

The bulk modulus of elasticity or the stiffness of the prior art metallic components is several orders of magnitude greater than that of the underlying bone. For example, cobalt-chrome and titanium which are typically used for orthopedic implants have a modulus of elasticity of 200,000 Newtons per millimeters squared ($N/mm^2$) and 110,000 $N/mm^2$ respectively. The densest cancellous bone in the proximal tibia is 350 $N/mm^2$, nearly three orders of magnitude less stiff than either of the metals. The mechanical stress and strain of the applied load at the flat interface of the component and proximal tibia causes abnormal bone growth and detrimentally affects the load carrying capability of the surrounding bone in the long term implant situation. Additionally, shear and tensile stress is experienced at the flat plateau interface of the proximal tibia which prevents biologic attachment of the component through bone ingrowth.

Therefore, it is a primary object of the present invention to provide a orthopaedic surgical implant device for replacing the articulating surface of a joint that distributes load and stresses onto the underlying bone as it is normally distributed in a natural joint.

It is also an object of the present invention to provide an orthopedic surgical implant device for replacing articulating surfaces of a joint that fosters normal bone growth in the proximal tibia so the bone can support the device.

It is still another object of the present invention to provide an orthopaedic surgical implant device that will remain attached to the bone for a relatively long time thereby improving implant longevity and permitting increased physical activity.

It is still a further object of the present invention to provide an orthopaedic surgical implant device having a stiffness factor more closely related to the stiffness of bone so that the device does not adversely affect the bone to which the device is attached.

It is still another object of the present invention to provide an orthopaedic surgical implant device having a curvature which minimizes bending stress in the device and prevents mechanical failure of the device.

It is another object of the present invention to provide an orthopaedic surgical implant device that produces a more physiological load application in the underlying bone by optimally reducing the cross-sectional mechanical properties of the device, particularly cross-sectional thickness and resistance to bending.

These and other objects of the present invention are achieved by an orthopaedic implant device designed to replace an articulating surface in a joint, wherein the device has a low stiffness factor which is capable of applying normal physiological load onto the underlying bone. The component is made of a material having a bulk modulus of elasticity nearer in magnitude to that of the underlying bone than has been that of previous components. Preferably the component will be manufactured from materials two orders of magnitude less stiff than high-strength metallic materials such as cobalt-chrome or titanium. To meet this objective, the component is preferably made from an advanced material such as polyetheretherketone, polysulfone or ultra-high molecular weight polyethylene (UHMPE). A low-stiffness factor is also achieved by a relatively thin component. The device is provided with curvature to minimize bending stress in the relatively thin component so that the component has sufficient mechanical strength to prevent stress induced failure. The curved configuration additionally provides a component having relatively low shear stress at the interface of the device and the bone.

A tibial implant device made in accordance with the present invention is a bicondylar concave-shaped unitary component made of an advanced material and having a related cross-sectional thickness that defines a normalized stiffness of less than 50,000 Newtons per millimeter which is more commonly expressed as 50,000 N/mm. The upper surface of the component is generally concave-shaped and designed in conjunction with the femur or femural implant to provide normal knee flexion and extension. The distal surface of the component is generally parallel to the upper surface, providing domical configurations on the distal surface in the medial and lateral regions of the component. Corresponding concave recesses in the proximal tibial bone surface are provided which receive the domical configurations on the distal surface of the implant when attached to the bone. Pegs or screws may be provided at the mid-sagittal region of the component to provide short term attachment. A porous thermoplastic coating on the distal surface of the component is preferred to promote bone ingrowth for long-term attachment.

DESCRIPTION OF THE DRAWINGS

In the accompanying drawings which form a part of the specification and are to be read in conjunction therewith and in which like reference numerals are used to indicate like parts in the various views:

FIG. 1 is an exploded perspective view of a tibial prosthesis of this invention attached to cover the resected surface of the proximal end of a prepared tibia.

FIG. 2 is a perspective view of the tibial prosthesis of FIG. 1 but shown in an inverted position to reveal details of construction.

FIG. 3 is a top plan view of the tibial prosthesis of FIGS. 1 and 2.

FIG. 4 is a detailed cross-sectional view taken along line 4—4 of FIG. 3, the prosthesis being shown attached to a resected surface of the proximal end of a tibia forming a part of a prepared human knee joint shown fragmentally in broken lines.

FIG. 5 is a view similar to FIG. 4 but taken along line 5—5 of FIG. 3.

DETAILED DESCRIPTION OF THE INVENTION

A principal feature of the present invention is that the prosthetic component defines a stiffness as closely related as is reasonably possible to that of bone so that the component will transfer relatively normal physiological loading to the tibia. Mechanical analysis accessing the structural relationship of bones in the natural joint can be used to determine an upper limit on acceptable prosthesis stiffness for normal physiological load application. A useful tool for this mechanical analysis is a computer intensive mathematics modeling technique known as finite element analysis (FEA) which is commonly used to evaluate complex mechanical systems. FEA has been used to assess the structural relationship of different tissues and the design of mechanical components used in prosthesis and fracture fixation. It is an outstanding tool for orthopaedic research because of its ability to handle highly irregular shapes and the intricate structural makeup of bone.

By analyzing the load distribution affected in the normal knee joint, inventors have determined that the stiffness of a tibial implant should not exceed specified limits. This stiffness can be expressed as a combination of the bulk modulus of elasticity of the material used to fabricate the device and the cross-sectional thickness of the device.

At any point in the implant device a line normal to the proximal and distal surface of the plate-like tibial device may be drawn and planes tangent to the surfaces at the intersection of the line with the surfaces are drawn. The elongation (δ) of a plate defined by the planes heretofore described under a prescribed load is a function of plate geometry and the material from which it is made.

$$\delta = \frac{PL}{AE}$$

where (P) is the force applied, (L) is the length of the plate, (A) is the cross-sectional area across which the load is applied and (E) is a bulk modulus of elasticity of the plane in the direction of the length of the plate. This equation can be rearranged to describe the stiffness (K) of the plate in any direction.

$$K = \frac{P}{\delta} = \frac{AE}{L}$$

The cross-sectional area (A) of the plate is derived from the plate thickness t and the width b.
So that $$A = bt$$

Thus, $$K = \frac{P}{\delta} = \frac{btE}{L}$$

A normalized stiffness $K_n$ for any point in the prosthesis as the length and width of the plate become infinitely small is defined as:

$$K_n = Et$$

This formulation of stiffness assumes that a curvature, to be described later, has been provided to the prosthesis which eliminates a significant amount of bending stress in the component so that subsequent loading is almost entirely compressive. It defines stiffness at a point and in any direction around that point and is applicable to homogeneous and composite materials.

It has been determined through mechanical analysis of the knee joint as heretofore described, that the preferred normalized stiffness for the tibial component $K_n$ should range from 300 N/mm to 50,000 N/mm (wherein N=Newtons) in order to provide normal physiological transfers of load to the tibia.

Any material having a bulk modulus of elasticity capable of defining a normalized stiffness of below 50,000 N/mm as heretofore defined and that is biocompatible can be used to fabricate the tibial component. Chromium cobalt and titanium materials are biocompatible and useful for surgical implantation, however, the modulus of elasticity for these materials is 200,000 N/mm² and 110,000 N/mm² respectively. Accordingly, the preferred normalized stiffness is not easily attainable utilizing these materials, because the component would have to be extremely thin. Although there are many materials which do have a low modulus of elasticity, other factors such as biocompatibility in particular limit the materials selection.

The implant device can be fabricated from advanced materials such as polysulfone and ultra-high molecular weight polyethylene which are currently utilized as low-friction bearing surfaces in prosthetic components and exhibit biocompatibility. These materials have shown utility as implant materials and are less stiff than the aforementioned metallic compounds. A preferred material is polyetheretherketone (PEEK) which is frequently available commercially from ICI Advanced Materials, Wilmington, Del. Although PEEK has not yet been approved for implant use, it is considered a good candidate. PEEK, having a modulus of elasticity (E) of 3,600 N/mm², provides a device having a normalized stiffness within the limit heretofore set and relatively close to the stiffness of bone. PEEK has outstanding material properties that make it desirable for use in prosthetic devices, including biocomcompatibility, resistance to a wide range of organic liquids and the capability of suffering no significant degradation in water environments. Additionally, this material has excellent creep, wear and abrasion resistance thereby providing a bearing surface having low friction for articulation with contacting bone, metal, or other plastic implants. By utilizing a low-friction material, a unitary component providing both a bearing surface and an attaching surface can be provided. The need for a two part tibial component is eliminated, although a two part component is not precluded if the combined stiffness of the components provides appropriate physiological load transfer to the underlying bone. PEEK is also preferred as a thermoplastic because it is processable by a wide range of conventional processes including injection molding.

The PEEK material may be impregnated with glass and carbon fibers to form short and long fiber composite materials adding strength to the device. However, this also adds stiffness to the device and the hydrolysis resistance and fatigue strength are somewhat diminished. Therefore, it is preferable to produce the device from PEEK that is not impregnated with such fibers. Rather, the necessary mechanical strength of the device is achieved by providing curvatures in the device.

Although selecting a material with a relatively low bulk modulus of elasticity for the material used in fabricating the component significantly holds stiffness to a low level, the cross-sectional thickness of the component can also be reduced to further provide the relatively low stiffness factor required to achieve load application approximating that of the natural joint. In some cases, the ability to reduce thickness of the component may be limited by the amount of bone mass removed, because a sufficient thickness is necessary to adequately replace the bone. To prevent stress induced bending related failures which can occur with a relatively thin component, the component should have a curved configuration so that a larger region of distributed contact stress is achieved and the bending stress in the component is minimized.

The accompanying drawings illustrate a tibial component designated generally by the reference numeral 10 embodying the principles of this invention. The tibial component is a unitary plate-like component of relatively uniform thickness having a substantially C-shaped or kidney shaped configuration. The outer periphery of the component corresponds generally to the outer periphery of the prepared proximal tibia 12, so that the tibial component covers nearly the entire proximal plateau of the surgically sectioned tibia.

The proximal tibia is resectioned by known surgical methods to remove the damaged articulating surface of the bone and to provide a generally flat resected bone surface 14 for component attachment. Curved recesses 16 and 18 on the medial and lateral regions respectively of the tibia are surgically created by removing a small amount of bone from the resected bone surface. The configuration of these recesses corresponds with curvatures provided on the medial and lateral regions of the distal surface of the tibial component, to be described later. The bone can be removed by any known methods, such as scraping with a convex tool.

A lower limit to prosthesis stiffness is defined by the strength of the material of which the prosthesis is manufactured. To prevent stress induced failures which accompany a low mechanical strength, curvatures which reduce bending stress are provided in the component. A significant portion of the mechanical stress in the tibial component stems from bending which can be greatly minimized by providing a device having concave curvatures 20 and 22 on the medial and lateral regions respectively of the proximal surface of the prosthesis as shown in FIG. 1. The distal surface of the prosthesis as shown in FIG. 2 is nearly parallel to the proximal surface forming domical related configurations 24 and 26 on the distal surface. The concave curvatures 20 and 22 provided in the proximal surface of the component correspond to receive the adjacent femural condyles as shown in FIGS. 4 and 5. The femural condyles represented as 30 and 32 interact and contact the proximal surface of the tibial component, rotating to simulate anatomical movement.

The domical configurations 24 and 26 on the distal surface of the component fit correspondingly into the recesses 16 and 18 cut from the resected tibial surface. This reduces shear and tensile stress at the interface of the component and tibia and additionally promotes bone ingrowth where a porous coating as explained more fully hereinafter is applied to the distal surface of the component.

The mid-sagittal region of the component is relatively flat having two holes 36 and 38 on the anterior and posterior region of the component respectively. Corresponding pegs or screws 40 are pressed or screwed through these holes into the proximal tibia surface to provide short term attachment of the component to the tibia. Short-term attachment of the concave-shaped tibial component to the bone can be accomplished by any other means which do not interfere with the long-term benefits provided by a prosthesis which is capable of providing normal physiological load transfer. This restriction will not necessarily preclude the use of any combination of pegs, posts or screws, however it is preferred that these devices not be used for attachment at the curved regions of the component.

Long-term attachment can be accomplished by a porous coating 42 provided on the distal surface of the component to stimulate bone ingrowth. The porous coating can be produced by several known methods, and is preferably made of a thermoplastic such as the thermoplastic coatings described in U.S. Pat. No. 4,167,794 issued to Spector, et al. because of their relatively low stiffnesses as compared to wire mesh. It is conceivable that the entire component could be fabricated from a porous material into which bone may grow. The concave-shape shape is a more suitable configuration for biologic ingrowth because it reduces shear stress imparted to the interface. If the component is manufactured from advanced composite materials, fiber orientation can be arranged to further optimize this configuration. The general stiffness and transverse properties can theoretically be tailored throughout the entire component to improve physiological load application and minimize shear stress at the bone interface. The concave shaped configuration does not however preclude the use of cement for long-term attachment, although biological bone ingrowth is preferred.

The tibial component is a single unitary piece having a relatively uniform thickness. The component is made from a low friction material having a low bulk modulus of elasticity, thereby providing both a good bearing surface for interaction with the articulating surface of adjacent bones in the joint and also transferring loads more nearly approximating the transfer of loads in natural physiological joint load applications. The component is also preferably relatively thin to help achieve the desired low stiffness characteristic. The curved configurations of certain regions of the device reduce bending stress so that mechanical failure of the relatively thin component is lessened or avoided. Additionally, the curvatures reduce shear stress at the interface of the bone and prosthetic component.

A tibial component embodying the principles of this invention can be formed by injection molding from polyetheretherketone (PEEK) provided by ICI Advanced Materials of Wilmington Del. This material has a modulus of elasticity of about 3,600 N/mm$^2$. With a cross-sectional thickness of approximately 2.0 millimeters at the domical contours, a normalized stiffness (Kn) of the component in any radial direction around the concave-shaped surfaces is defined by Et which is about 7,200 N/mm. This stiffness nearly matches the normalized stiffness of subchondral bone. Subchondral bone is a thin layer of bone of the proximal tibia. It is approximately 1 mm thick and has a modulus of elasticity of 7,000 N/mm$^2$. Its normalized stiffness is therefore 7,000 N/mm. The concave curvatures reduce bending stress thereby permitting a relatively low thickness dimension while maintaining sufficient mechanical strength for the component. This component is considered entirely adequate for achieving the objectives of the invention as set out above.

It will be understood that certain features and subcombinations of this invention are of utility and may be employed without reference to other features and subcombinations. For instance, reduction of stiffness to provide normal physiological load application is contemplated for any articulating surface replacement. Additionally, other component configurations are contemplated meeting the stiffness requirements in accordance with this invention.

Since many possible embodiments may be made of the invention without departure from the scope thereof, it is to be understood that all matter herein set forth or shown in the accompanying drawings is to be interpreted as illustrative and not in a limiting sense.

What is claimed is:

1. A prosthesis for replacing bone material of a natural condylaris joint, the prosthesis comprising:
   a plate-like component having first and second opposed, generally planar surfaces, the first surface being formed with at least one concavity and the second surface being substantially parallel with the first surface, the thickness of the component being substantially uniform across the area of the concavity;

the component being formed of a material having a modulus of elasticity which, when multiplied by the thickness of the component within the area of the at least one concavity, defines a stiffness less than about 50,000 N/mm so that the transfer of a load through the component in a direction generally normal to the first and second surfaces simulates transfer of the same load through the bone material of the natural joint which the prosthesis is adapted to replace.

2. A prosthesis as set forth in claim 1, wherein the stiffness defined by the component is within the range of 300 N/mm to 50,000 N/mm.

3. A prosthesis as set forth in claim 1, wherein the material forming the component is selected from the group consisting of polyetheretherketone, polysulfone and ultra high molecular weight polyethylene.

4. A prosthesis as set forth in claim 1, wherein the component is formed of a porous thermoplastic material.

5. For use in a joint between a pair of articulating bones, one of which presents a condyle having a curved outer surface defined by a first curvature, and the other of which opposes the condyle, a prosthesis for replacing resected bone material of the bone opposing the condyle, the resected bone material to be replaced by the prosthesis being characterized by a first predetermined stiffness, the prosthesis comprising:
   a plate-like component having a generally planar bearing surface formed with a concavity having a curvature which receives the curvature of the condyle, and a generally planar attachment surface substantially parallel with the bearing surface, the thickness of the component being substantially uniform across the area of the concavity,
   the component being formed of a material having a modulus of elasticity which, when multiplied by the thickness of the component within the area of concavity, defines a stiffness substantially equal to the predetermined stiffness of the bone material replaced by the prosthesis so that the transfer of a load through the component in a direction generally normal to the bearing and attachment surfaces simulates transfer of the same load through the bone material replaced by the prosthesis.

6. A prosthesis as set forth in claim 5, wherein the attachment surface includes a porous coating to promote biological ingrowth.

7. A prosthesis as set forth in claim 5, wherein the stiffness defined by the component is within the range of 300 N/mm to 50,000 N/mm.

8. A prosthesis as set forth in claim 5, wherein the material forming the component is selected from the group consisting of polyetheretherketone, polysulfone and ultra high molecular weight polyethylene.

9. A prosthesis as set forth in claim 5, wherein the component is formed of a porous thermoplastic material.

10. For use in a knee joint between a femur presenting a pair of condyles each having a curved outer surface defined by a predetermined curvature, and a tibia opposing the condyles, a prosthesis for replacing resected subchondral bone material of the tibia, the prosthesis comprising:
    a plate-like tibial component having a generally planar bearing surface formed with a pair of concavities each opposing one of the condyles and having a curvature which receives the curvature of the opposing condyle, and a generally planar attachment surface substantially parallel with the bearing surface, the thickness of the component being substantially uniform across the areas of the concavities,
    the tibial component being formed of a material having a modulus of elasticity which, when multiplied by the thickness of the tibial component within the areas of the concavities, defines a stiffness less than about 50,000 N/mm so that the transfer of a load through the component in a direction generally normal to the bearing and attachment surfaces simulates transfer of the same load through the subchondral bone material of the natural knee joint.

11. A prosthesis as set forth in claim 10, wherein the attachment surface of the tibial component includes a porous coating to promote biological ingrowth.

12. A prosthesis as set forth in claim 10, wherein the stiffness defined by the tibial component is within the range of 300 N/mm to 50,000 N/mm.

13. A prosthesis as set forth in claim 10, wherein the material forming the tibial component is selected from the group consisting of polyetheretherketone, polysulfone and ultra high molecular weight polyethylene.

14. A prosthesis as set forth in claim 10, wherein the tibial component is formed of a porous thermoplastic material.

15. A prosthesis as set forth in claim 10, wherein the stiffness defined by the tibial component is about 7000 N/mm.

* * * * *